United States Patent [19]

Stables et al.

[11] 4,205,165

[45] May 27, 1980

[54] PROCESSING OF CEPHALOSPORIN C

[75] Inventors: Harry C. Stables; Kenneth Briggs, both of Ulverston, England

[73] Assignee: Glaxo Group Limited, London, England

[21] Appl. No.: 965,586

[22] Filed: Dec. 1, 1978

[30] Foreign Application Priority Data

Dec. 6, 1977 [GB] United Kingdom ............... 50772/77

[51] Int. Cl.$^2$ ............................................ C07D 501/12
[52] U.S. Cl. ........................................ 544/20; 424/246
[58] Field of Search .......................................... 544/20

[56] References Cited

U.S. PATENT DOCUMENTS

| | | | |
|---|---|---|---|
| 3,184,454 | 5/1965 | Abraham et al. | 260/243 |
| 3,467,654 | 9/1969 | McCormick | 544/20 |
| 3,725,400 | 4/1973 | Voser | 544/20 |
| 3,983,108 | 9/1976 | Pines | 544/20 |

FOREIGN PATENT DOCUMENTS 50-76486  12/1975  Japan.
968324  9/1964  United Kingdom.

*Primary Examiner*—Nicholas S. Rizzo
*Attorney, Agent, or Firm*—Bacon & Thomas

[57] ABSTRACT

A process for the recovery of cephalosporin C comprises (a) contacting a fermentation broth containing cephalosporin C with an anion exchange resin which is either a weak-base resin in the weak acid salt form or free base form or a strong-base resin in the weak acid salt form, to obtain a weakly acidic percolate containing said cephalosporin C from which anions of strong acids present in said broth have been removed;

(b) contacting said percolate with a strong cation exchange resin in the acid form, whereby cations in said resulting solution are replaced by protons and said cephalosporin C remains in the substantially deionized percolate; and (c) adsorbing cephalosporin C from said percolate onto a weak-base anion exchange resin.

6 Claims, No Drawings

PROCESSING OF CEPHALOSPORIN C

This invention concerns the processing of cephalosporin C and more particularly concerns a process for the recovery of cephalosporin C from a fermentation broth.

The extraction of cephalosporin C from fermentation broths is a problem of long standing, to which many solutions have been proposed. Cephalosporin C is produced in dilute aqueous solution; the difficulty of recovery is caused by the high water-solubility and zwitterionic nature of cephalosporin C and the presence of other materials including those having similar chemical and physical properties. These contaminants include many ionic species. In one method of isolation, basic ion exchange resins are used for selective adsorption of cephalosporin C. However, a particular problem which has been experienced when attempting to adsorb cephalosporin C directly onto an ion exchange resin is that the fermentation broth contains other materials, particularly considerable quantities of inorganic ions, which lead to unsatisfactory adsorption on the resin, unacceptably high percolate losses, and a low, inefficient use of the resin capacity for the cephalosporin C.

Methods such as selective adsorption of cephalosporin C onto charcoal or alumina have been employed to separate cephalosporin C from the inorganic ions. Adsorption onto charcoal or alumina results in substantial losses of cephalosporin C because of irreversible adsorption and/or decomposition; such losses may often be about 10–20%. Also the adsorption process is time consuming.

The recovery of cephalosporin C is beset with so many difficulties that some workers have preferred to modify the antibiotic enzymically or chemically at an early stage in the recovery process to a derivative having more favourable physico-chemical properties, before attempting to extract it.

We have now found that the treatment of the fermentation broth with a specific combination of ion exchange resins can form a valuable part of a process for the recovery of cephalosporin C.

In one aspect, our invention provides a process for the recovery of cephalosporin C which comprises (a) contacting a fermentation broth containing cephalosporin C with an anion exchange resin which is either a weak-base resin in the weak acid salt form or free base form or a strong-base resin in the weak acid salt form, to obtain a weakly acidic percolate containing said cephalosporin C from which anions of strong acids present in said broth have been removed; (b) contacting said percolate with a strong cation exchange resin in the acid form, whereby cations in said resulting solution are replaced by protons and said cephalosporin C remains in the substantially deionised percolate; and (c) adsorbing cephalosporin C from said percolate onto a weak base anion exchange resin.

Before being treated by our process, the broth is preferably filtered. Desirably the broth is acidified to lower the pH from neutrality to a value in the range 1 to 6, preferably 2 to 5. An increase in acidity is beneficial in assisting precipitation of proteinaceous materials. It is especial preferred to acidify prior to filtration, advantageously in the presence of a filter aid. Precipitated material may be removed by filtration, preferably on a rotary vacuum filter, or by centrifugation or other suitable techniques.

In the absence of prior acidification, the fall in pH which occurs in the presence of the strong cation exchange resin in step (b) results in an increased precipitation of proteinaceous material, which can impede subsequent processing.

However, it should be remembered that the addition of inorganic acid to the broth will increase the inorganic anion load of the broth and this will require an increased proportion of anion exchange resin for its removal in step (a) of the process. Moreover, when a weak-base resin in the free base form is used in step (a) it may be necessary to add a weak acid to control an upward pH excursion in this step. This acid is conveniently added prior to filtration. Optimum acidification should be selected with these factors in mind.

The mycelium and proteinaceous material filtered off should be washed to avoid excessive loss of antibiotic, but liquid volumes should desirably be kept to a minimum to facilitate further processing.

The broth may be brought into contact with the anion exchange resin in step (a) in any desired way, most suitably by passing through a column or bed of granular resin, e.g. in the conventional bead form. When the broth is essentially free of particulate matter, either upflow or downflow techniques may be used. Non-filtered broth is preferably passed through the resin column or bed from the base upwards, using a fluidised bed or pulsed bed system.

The anion exchange resin is preferably a weak base anion exchange resin, for example an amino-polystyrene, amino-polyacrylic or amino-phenolic resin which may be cross-linked. A suitable amino-polystyrene resin is Amberlite IR-45, based on polystyrene cross-linked with divinylbenzene. An amino-polyacrylic resin which may be used is Amberlite IRA-68. Suitable amino-phenolic resins are Amberlite IR-4B and Deacidite E. These resins all have polyamine functionality. The weak base anion exchange resin is preferably used in the weak acid salt form e.g. as the acetate. Weak base anion exchange resins are more economically regenerated than strong base anion exchange resins. However strong base anion exchange resins may be used, e.g. Amberlite IRA-400 or IRA-900, which resins comprise a styrene/divinyl benzene skeleton substituted with quaternary ammonium groups. Strong base anion exchange resins, if used, must be employed in the salt form, as salts of a weak acid.

The anion exchange resin is used as a weak acid salt form or as a free base to remove the anions of strong acids present in the broth. When the weak acid salt form of resin is used, the weak acid anion appears in the precolate and will not impede subsequent purification. The weak acid is preferably a carboxylic acid having a pKa value in the range 2–5; the weak acid should be selected so as not to compete significantly with cephalosporin C for adsorption on the weak-base anion exchange resin in step (c), and for this reason we tend to prefer acids having pKa values above 3.5. The preferred weak acid is acetic acid.

When the free base form of the anion exchange resin is used, the feedstock must be sufficiently acidic to protonate the resin. It is also necessary that weak acid anions are present to moderate the rise in pH which would otherwise occur on removal of protons by the resin. If a sufficient concentration of weak acid anions is not already present in the feedstock, this may be provided by the addition of a suitable weak acid as discussed above, e.g. acetic acid, prior to loading the resin.

Thus in either case, whether the resin is in the weak acid salt form or in the free acid form, the percolate contains a weak acid/weak acid salt buffer system which maintains a weakly acidic pH of about 6.

For optimum efficiency, the capacity of the anion exchange resin should be so matched to the volume and ionic content of the broth that at the conclusion of step (a) the resin is substantially saturated with strong acid anions. The cephalosporin C initially adsorbed by the resin is thus displaced by strong acid anions and appears in the percolate.

An advantageous mode of performing step (a) will now be described.

While the percolate containing cephalosporin C is substantially free of anions of strong acids such as sulphate, chloride and phosphate, this percolate is directed to a column or bed of strong cation exchange resin as described hereinafter for step (b). When the anions of strong acids such as sulphate, chloride and phosphate begin to appear in the percolate, wherein they may be detected by standard analytical methods, the percolate is redirected to a second similar column of anion exchange resin. When the first column is saturated with anions of strong acids, the flow of broth is directed to the second column of anion exchange resin which also receives water washings from the first column containing interstitial broth. The percolate from the second column is again directed to a column or bed of strong cation exchange resin as described hereinafter for step (b). The resins may be regenerated by standard methods.

In step (b) the percolate mentioned above is then contacted with a strong cation exchange resin in the acid form. This resin also is preferably used as a column or bed, using either downflow or upflow techniques, e.g. a fluidised bed or pulsed bed upflow technique.

The strong cation exchange resin will contain strongly acidic groups, such as sulphonate or phosphate groups. The preferred resin is a cross-linked polystyrene sulphonic acid resin such as Amberlite IR-120, Dowex 50 or Zeo-karb 225. Exhaustion of the cation exchange resin may be detected e.g. by monitoring the pH or conductivity of the percolate. Two or more columns of strong cation exchange resin may be used in an analogous manner to that described above for use of the anion exchange resin in step (a). The resin may be regenerated by treatment with a strong acid.

It is essential that the broth is (a) first contacted with the anion exchange resin and (b) subsequently contacted with the strong cation exchange resin. When the broth is contacted with the first resin in a weak-acid salt form or when a weak base resin is used in the free base form with weak acid anions present in the feedstock, as explained above a weak acid/weak acid salt buffer system is formed which stabilises the acidity at about pH 6. Subsequent contact with the strong cation exchange resin produces a weak acid from the weak acid salt, which reduces the pH to about 2.5 to 3.0. If the order of treatment is reversed, contact of the broth with a strong cation exchange resin in the first stage will lower the pH to a value less than 1 due to the formation of highly ionised strong acids before treatment with the anion exchange resin. At this pH, the cephalosporin C is protonated and as a cation begins to be adsorbed to a significant extent by the cation exchange resin, and moreover degradation is quite rapid below pH 1. This order of treatment would produce a significantly inferior efficiency of recovery.

In the process of our invention the percolate entering step (c) is essentially a solution in water of cephalosporin C, non-ionic impurities and a weak acid. This percolate may be obtained from the initial broth much more rapidly and efficiently than by processes involving selective adsorption and elution of cephalosporin C, e.g. from carbon. Thus opportunity for the decomposition of the cephalosporin C is reduced. Moreover no organic solvents are required in the initial stages of the recovery, when large volumes of liquid have to be processed.

In step (c) the cephalosporin C is adsorbed on a weak-base anion exchange resin, for example of the type used in step (a), such as Amberlite IRA-68. The resin is preferably used in the weak acid salt (e.g. acetate) form. Because the percolate has been largely deionised, the resin can adsorb a much larger amount of cephalosporin C from the percolate than from an equivalent volume of filtered broth.

Further purification and isolation of the cephalosporin C can be performed relatively easily by conventional techniques. For example, after elution from the weak-base anion exchange resin, e.g. with an inorganic or organic salt solution at pH 4–7, such as sodium or potassium acetate, the cephalosporin C can e.g. be precipitated as a salt by the addition of water-miscible organic non-solvents such as acetone; or precipitated as a sparingly soluble microcrystalline heavy metal complex, e.g. as a complex with copper, mercury, lead, cadmium, manganese, iron, cobalt, nickel or especially zinc.

In order that our invention may be better understood, the following Examples are given by way of illustration only.

EXAMPLE 1

A fermentation broth containing cephalosporin C was filtered at its natural pH (about 6) using a suitable filter aid. The filtrate obtained was diluted with water to give a loading solution containing about 7.3 g of cephalosporin C per liter.

This solution was passed downflow over three ion-exchange resin columns in series:

Column I: One liter of Amberlite IRA 68 anion exchange resin in the acetate form.

Column II: One liter of Zeo-Karb 225 cation exchange resin in the acid (hydrogen) form.

Column III: 400 ml of Amberlite IRA 68 anion exchange resin in the acetate form.

The loading solution was passed at 800 ml per hour until sulphate ion was detected in the percolate from column I.

Columns II and III were washed in series with 2.8 liters of water at a flow rate of 800 ml/hour. Particulate matter was removed from column III by passing 850 ml of water upflow at a rate sufficient to expand the resin bed. 5.9% of the original input cephalosporin C was found to be present in the combined percolates and washes from column III.

Column III was then eluted downflow with 0.1 molar potassium acetate solution adjusted to pH 6.5 with acetic acid. The rich eluate was collected between $a_D$ 0.5°–0.5°. This eluate had a concentration of 16.8 grammes of cephalosporin C per liter (by fluorimetric assay) and contained 83% of the cephalosporin loaded as filtered broth.

EXAMPLE 2

A fermentation broth containing cephalosporin C was acidified to pH 4.5 using sulphuric acid. It was then filtered using a suitable filter aid and the filtrate was diluted with water to give a loading solution containing about 7.0 g of cephalosporin C per liter.

This loading solution was passed downflow over two ion-exchange resin columns in series:

Column I: 400 ml of Amberlite IRA 68 anion exchange resin in the acetate form; bed length of column 62 cm.

Column II: 400 ml of Zeo-Karb 225 cation exchanger in the acid (hydrogen) form; bed length of column 62 cm.

The loading solution was passed at 400 ml per hour until sulphate ion was detected in the percolate from column I.

Column I was then washed with 800 ml of water. The washes were recovered and assayed for cephalosporin. This amount was deducted to calculate the total amount of cephalosporin C loaded.

Column II was washed with 800 ml water. These washes combined with the percolates from column II were found to contain 94% of the nett cephalosporin C loaded.

3.0 liters of the combined solution was passed over a third column:

Column III: 200 ml Amberlite IRA 68 anion exchange resin in the acetate form; bed length of column 56 cm.

The combined solution was passed through the column at 400 ml per hour, then the column was washed with 400 ml of water. The combined washes and percolates were found to contain 2% of the cephalosporin C loaded onto column III. Column III was then eluted downflow with 0.1 molar potassium acetate solution adjusted to pH 6.5 with acetic acid. The rich eluate was collected between $\alpha_D$ 0.5°–0.5°. This eluate had a concentration of 14.4 g of cephalosporin C per liter (by fluorimetric assay) and contained 96% of the cephalosporin C loaded onto column III.

We claim:

1. A process for the recovery of cephalosporin C which comprises
    (a) contacting a fermentation broth containing cephalosporin C with an anion exchange resin which is either a weak-base resin in the weak acid salt form or free base form or a strong-base resin in the weak acid salt form, to obtain a weakly acidic percolate containing said cephalosporin C from which anions of strong acids present in said broth have been removed;
    (b) contacting said percolate with a strong cation exchange resin in the acid form, whereby cations in said resulting solution are replaced by protons and said cephalosporin C remains in the substantially deionised percolate; and
    (c) adsorbing cephalosporin C from said percolate onto a weak-base anion exchange resin.

2. A process according to claim 1 wherein said fermentation broth is acidified to a pH in the range 2 to 5 and precipitated material is removed prior to contacting with the anion exchange resin in step (a).

3. A process according to claim 1 or 2 wherein said anion exchange resin in step (a) is a weak-base resin in the acetate form.

4. A process according to claim 1 or 2 wherein said anion exchange resin in step (a) is a weak-base resin in the free base form and wherein the feedstock to said resin contains sufficient acetic acid to ensure that said percolate is weakly acidic.

5. A process according to claim 1 wherein said weak-base anion exchange resin in step (c) is used in the acetate form.

6. A process according to claim 1 including the step of eluting the cephalosporin C from said weak-base anion exchange resin with an inorganic or organic salt solution at pH 4 to 7 and subsequently precipitating cephalosporin C from the eluate as a salt or complex thereof.

* * * * *